United States Patent
Samuels

(10) Patent No.: US 10,132,745 B2
(45) Date of Patent: Nov. 20, 2018

(54) ENCODED CALIBRATION DEVICE AND SYSTEMS AND METHODS THEREOF

(71) Applicant: Mark A. Samuels, Johns Creek, GA (US)

(72) Inventor: Mark A Samuels, Johns Creek, GA (US)

(73) Assignee: Mark A. Samuels, Norcross, GA (US)

( * ) Notice: Subject to any disclaimer, the term of this patent is extended or adjusted under 35 U.S.C. 154(b) by 341 days.

(21) Appl. No.: 14/774,982

(22) PCT Filed: Mar. 12, 2014

(86) PCT No.: PCT/US2014/024465
§ 371 (c)(1),
(2) Date: Sep. 11, 2015

(87) PCT Pub. No.: WO2014/159620
PCT Pub. Date: Oct. 2, 2014

(65) Prior Publication Data
US 2016/0018260 A1    Jan. 21, 2016

Related U.S. Application Data

(60) Provisional application No. 61/852,176, filed on Mar. 15, 2013, provisional application No. 61/851,934, filed on Mar. 14, 2013.

(51) Int. Cl.
*G01C 19/00* (2013.01)
*G01N 21/27* (2006.01)
*G01J 5/52* (2006.01)
*G06F 11/30* (2006.01)
*G01R 35/00* (2006.01)

(52) U.S. Cl.
CPC ............ *G01N 21/278* (2013.01); *G01J 5/522* (2013.01); *G01R 35/005* (2013.01)

(58) Field of Classification Search
CPC .................................................. G01N 21/278
See application file for complete search history.

(56) References Cited

U.S. PATENT DOCUMENTS 8,300,222 B2 * 10/2012 Jung ...................... A61C 19/04
356/402
2008/0114228 A1 * 5/2008 McCluskey ........ A61B 5/14514
600/365

\* cited by examiner

*Primary Examiner* — Phuong Huynh
(74) *Attorney, Agent, or Firm* — Schwegman Lundberg & Woessner, P.A.

(57) ABSTRACT

Implementations described herein comprise systems, apparatus and methods for calibration of imaging, radio frequency or spectroscopic instruments that can be used to validate, calibrate or confirm the calibration thereof. In one aspect, a calibration target is provided. The calibration target has a tissue interface and an instrument interface. The instrument interface has a first storage means having a first set of calibration data encoded therein and a second storage means having a second set of calibration data encoded therein. The first storage means and the second storage means are selected to comprise different storage modalities. Both the first and second set of calibration data are necessary to perform calibration of the instrument.

19 Claims, 2 Drawing Sheets

ENCODED CALIBRATION DEVICE AND SYSTEMS AND METHODS THEREOF

CROSS-REFERENCE TO RELATED APPLICATIONS

This application claims priority to and the benefit of Provisional Application Ser. No. 61/851,934, filed or Mar. 14, 2013 filed on Mar. 14, 2013 and U.S. Provisional Application Ser. No. 61/852,376 filed on Mar. 15, 2013 both entitled "Encoded Calibration Disposable." which applications are hereby incorporated in their entire in this document by reference.

BACKGROUND OF THE INVENTION

The Field of the Invention

Implementations described herein relate generally to apparatus, systems and methods for calibration of imaging, radio frequency or spectroscopic instruments that can be used to validate, calibrate or confirm the calibration thereof.

RELATED ART

Many measurement systems require that calibrations be performed on a periodic basis in order to compensate for performance differences present at manufacture as well as drift in instrument performance and response over time. Calibration techniques can involve measuring the response of a test target that has characteristics that remain stable with time and over a range of environmental conditions and using that information to normalize or correct the instrument response. Calibration techniques can be used to compensate for variations between instruments and changes that an individual instrument may experience over its working lifetime. Often such measurement systems most be periodically calibrated and sometimes must be calibrated prior to each and every use. This calibration becomes especially important when measurements are made for medical or other critical applications.

Radiation based measurement systems, i.e., systems that send electromagnetic radiation to the tissue or material to be measured and then detect the return radiation such as spectroscopy, can require frequent calibration. Radiation measuring systems are currently used for a wide variety of purposes including evaluation of tissue or materials. These measuring systems can require calibration for a variety of reasons such as variations in the radiation source intensity, changes in spectral characteristics of the tissue or material, component aging and cleanliness, changes in temperature, radiation detector sensitivity changes, and electronic drifting. In fact, calibration of spectroscopic instruments is well known in the field of spectroscopy.

Calibration targets have been used in medical devices for reflectance-based instruments and some have even been configured to be disposable. Ideally, Calibration targets have tightly controlled properties in order to ensure accurate results from the instrument being calibrated. Such tight tolerances on the properties of the calibration target can measurably increase the cost of a calibration target, rendering disposable calibration targets impractical due to cost. For example, a 2" square standardized Spectralon target from Labsphere can cost about $760.00. In addition, a calibrated glass 1951 Air force resolution target from Thor Labs can cost over $160.00. Further, conventional commercial calibration targets are not suited for polarization-sensitive instruments because they are not sensitive to polarization and, therefore, cannot test the polarization characteristics of a polarization sensitive instrument.

Accordingly, a need exists for improved apparatus, systems and methods for validating both disposable and non-disposable calibrations targets used to calibrate or confirm the proper operation and accuracy of a variety of imaging, RF or spectroscopic instruments. Additionally, a need exists for calibration targets that encode calibration parameters for an instrument to read as well as instruments capable of reading information encoded on a calibration target and capable of adjusting or correcting output based on the those calibration parameters and measurement of the other properties of the calibration target.

SUMMARY

It is to be understood that this summary is not an extensive overview of the disclosure. This summary is exemplary and not restrictive, and it is intended to neither identify key or critical elements of the disclosure not delineate the scope thereof. The sole purpose of this summary is to explain and exemplify certain concepts of the disclosure as an introduction to the following complete and extensive detailed description.

In one aspect the present disclosure provides a calibration target having a tissue interface, and an instrument interface. The instrument interface can have a first storage means having a first set of calibration data encoded therein and a second storage means having a second set of calibration data encoded therein. In one aspect, the first and second storage means can comprise different storage modalities. It another aspect, both the first and second set of calibration data are necessary to perform calibration of an instrument.

The present disclosure further provides for a system comprising a calibration target comprising a first set and a second set of calibration data, an instrument having at least one sensor operable to read at least one of the first and second set of calibration data on the calibration target and perform a calibration based on the calibration data, wherein both the first and second set of calibration data are required to perform calibration of an instrument.

Additional features and advantages of exemplary implementations of the invention be set for in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTIONS OF THE DRAWINGS

The accompanying drawings, which are incorporated in and constitute a part of this specification, illustrate aspects and together with the description, serve to explain the principles of the methods and systems.

DESCRIPTION OF THE INVENTION

Figure 1:
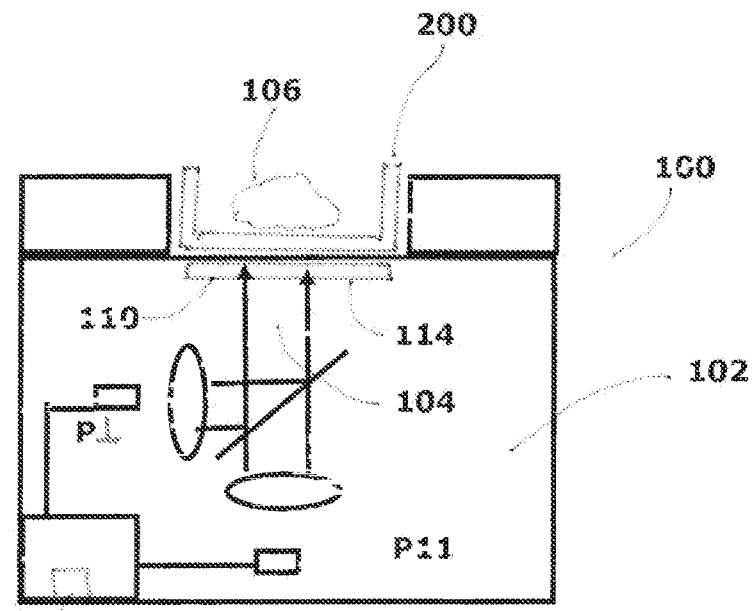
FIG. 1 illustrates an implementation of one exemplary aspect of a system for validating calibration targets for imaging or spectroscopic instruments.

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. To this end, those skilled in the relevant art will recognize and appreciate that many changes can be made to the various aspects of the invention described herein, while still obtaining the beneficial results described herein. It will also be apparent that some of the desired benefits described herein can be obtained by selecting some of the features described herein without utilizing other features. Accordingly, those who work in the art will recognize that many modifications and adaptations to the present invention are possible and can even be desirable in certain circumstances and are a part described herein. Thus, the following description is provided as illustrative of the principles described herein and not in limitation thereof.

Reference will be made to the drawings to describe various aspects of one or more implementations of the invention. It is to be understood that the drawings are diagrammatic and schematic representations of one or more implementations, and are not limiting of the present disclosure. Moreover, while various drawings are provided at a scale that is considered functional for one or more implementations, the drawings are not necessarily drawn to scale for all contemplated implementations. The drawings thus represent an exemplary scale, but no inference should be drawn from the drawings as to any required scale.

In the following description, numerous specific details are set forth in order to provide a thorough understanding described herein. It will be obvious, however, to one skilled in the art that the present disclosure may be practiced without these specific details. In other instances, well-known aspects of spectroscopic instrumentation and calibration thereof have not been described in particular detail in order to avoid unnecessarily obscuring aspects of the disclosed implementations.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps, "Exemplary" means "an example of" and is not intended to convey an indication of a preferred or ideal aspect. "Such as" is not used in a restrictive sense, but for explanatory purposes.

As used in the specification and appended claims, the term "disposable" and variations of this word should be construed to mean "lower cost." Additionally, since the concept of disposability is an economic one and anything can be disposed of, any reference to a "disposable" device should also be construed to apply to "non-disposable" device.

As used in the specification and the appended claims, the terms "image-based code", "bar code", "matrix code", "QR code" and variations thereof should be interpreted to cover all forms of linear barcodes, two dimensional barcodes and matrix codes including, for example and without limitation, Codabar, Code 25, Code 11, Code 39, Code 93, Code 123, CPC Binary, DUN 14, BAN 2, EAN 5, EAN 8, EAN 13, facing identification mark, GS1-128, GS1 DataBar, Intelligent Mail barcode, ITF-14, JAN, latent image barcode, MSI, Pharmacode, PLANET, Plessey, PostBar, POSTNET, RM4SCC/KIX, Telepen, U.P.C., 3-DI, ArrayTag, AugTag, Aztec Code, Small Aztec Code, Codablock, Code 1, Code 16K, Code 49, ColorCode, Color Construct Code, Compact Matrix Cole, CP Code, CyberCode, d-touch, DataGlyphs, Data Matrix, Datastrip Code, digital paper, Dot Code A, EZcode, Grid Matrix Code, HD Barcode, High Capacity Color Barcode, HueCode, INTACTA.CODE, InterCode, JAGTAG, MaxiCOde, mCode, MiniCode, MicroPDF417, MMCC, NexCode, Nintendo e-Reader Dot Code, Optar, PaperDisic, PDF417, PDMark, QR Code, QuickMark Code, Water Code, Secure Seal, SmartCode, Snowflake Code, ShotCode, SPARQCode, SuperCode, TrillCode, UltraCode, UnixCode, VeriCode, VS Code and the like.

As used in the specification and appended claims, the term "dongle" should be construed to refer to a relatively small piece of hardware that attaches to a device such as, but not limited to, an instrument, computer, TV, and the like, and that, when attached, provides code that enables additional functions such as, for example and without limitation, copy protection, audio, video, games, data, and the like by providing a code that is needed by the device to proceed. The code can be stored in the dongle or the code can be generated by the dongle from inputs received from the device. Typically, these additional functions are only available when the dongle is attached to the device.

As used in the specification and appended claims, the term "RFID" should be construed to refer to "the wireless non-contact use of radio-frequency electromagnetic fields to transfer data for the purposes of automatically identifying and tracking tags attached to objects." Further, as used herein, "RFID tags" contain electronically stored information and can be powered and read via known methods. For example and without limitation, some RFID tags can be powered by and read at short ranges (a few meters) via magnetic fields (electromagnetic induction), and then can act as a passive transponder to emit microwaves or UHF radio waves (i.e., electromagnetic radiation at high frequencies) and other RFID tags can use a local power source such as a battery, and can operate at hundreds of meters. Unlike a bar code, the RFID tag does not necessarily need to be within line of sight of the reader, and may be embedded in the tracked object.

As used in the specification and appended claims, the term "encryption" should be construed to refer data encryption standard ("DES"), advanced encryption standard ("AES") and the like.

Disclosed are components that can be used to perform the disclosed methods and systems These and ether components are disclosed herein, and it is understood that when combinations, subsets, interactions, groups, etc of these components are disclosed that while specific reference of each various individual and collective combinations and permutation of the may not be explicitly disclosed each is specifically contemplated and described herein, fir all methods and systems. This applies to all aspects of this application including, but not limited to, steps in disclosed methods. Thus, if there are a variety of additional steps that can be predefined it is understood that each of these additional steps can be predefined with any specific aspect or combination of aspects of the disclosed methods.

Reference will now be made to the drawings to describe various aspects of one or more implementations of the invention. It is to be understood that the drawings are diagrammatic and schematic representations of one or more implementations, and are not limiting of the present disclosure. Moreover, while various drawings are provided at a scale that is considered functional for one or more implementations, the drawings are not necessarily drawn to scare for all contemplated implementations. The drawings thus represent an exemplary scale, but no inference should be drawn from the drawings as to any required scale.

Implementations disclosed herein comprise apparatus, systems and methods for calibration of imaging, radio frequency (RF) and spectroscopic instruments used to validate, calibrate or confirm the calibration thereof. In further, implementations of the present disclosure comprise apparatus, systems and methods for use with polarization-sensitive instruments. In other aspects, the present disclosure provides for calibration targets encoded with calibration data comprising validation codes, calibration constants or calibration ranges. In a further aspect, the present disclosure provides for calibration targets having the encoded information distributed across at least two of an image-based code, an RFID tag, an electrical contact or an optical communication means. In even further aspects, the present disclosure provides for calibration targets having polarization-encoded information.

In other aspects, the present disclosure provides a means for instruments to read validation codes and calibration constants or ranges encoded on at least one of an image-based code, an RFID tag, an electrical contact or an optical communications means. In further aspects, the present disclosure provides a means for instruments to read polarization-encoded information.

In yet other aspects, the present disclosure provides for a pathology or sample tray to be integrated with a calibration target comprising calibration data.

In the following description, numerous specific details are forth in order to provide a thorough understanding described herein, it will be obvious, however, to one skilled in the art that the present disclosure may be practiced without these specific details. In other instances, well known aspects of spectroscopic instrumentation and calibration thereof have not been described in particular detail in order to avoid unnecessarily obscuring aspects of the disclosed implementations.

Turning now to FIG. 1, an implementation of one exemplary aspect of a system for validating calibration targets for imaging of spectoscopic instruments is illustrated. The system 100 includes an instrument 102 which outputs electromagnetic radiation 134 and receives and analyzes radiation. In one aspect, the radiation is reflected back towards the device by a material or tissue 106 being measured, or is generated by the material or tissue 106 in response to the radiation output by the instrument 102. In another aspect, the radiation is reflected or scattered back by an intervening surface 114 on the calibration target 200. In yet another aspect, the intervening surface 14 is configured to emit fluorescent or luminescent radiation when exposed 10 electromagnetic radiation from the instrument 102. The tissue 106 can be positioned in a pathology tray 200 that comprises a calibration target. One skilled in the art will appreciate that, with regard to electromagnetic radiation 104, the instrument 102 can be an optical spectrometer, optical imaging device or, alternatively, an RF spectrometer, an RF imaging device or any other radiation measuring instrument that outputs radiation to a material or tissue 106, then measures some portion of a return signal. While implementations disclosed herein discuss the inventive embodiments of the present disclosure with regard to spectroscopy, it should be understood that any other radiation measuring instrument that outputs radiation to a material or tissue then measures some portion of a return signal falls within the scope of the present disclosure. Optionally, a shield 110 can serve as a barrier between the instrument 102 and a material or tissue 106 to be measured, and can function to reduce potential contamination of the material or tissue.

In another aspect, the system 100 provides for storage of spectral characteristics or calibration data on a calibration target. In one aspect, the system 100 is configured to validate a calibration target prior to performing a calibration. In light of the present disclosure, one skilled in the art will appreciate that the system 100 described herein can eliminate the need to carefully control the spectral characteristics of the calibration target material since data on the exact spectral characteristics expected can be encoded into each calibration target. Also, the system 100 described herein can be configured to prevent unauthorized use of the instrument 102, subsequent use of used disposable calibration targets, and use of counterfeit or other unsuitable calibration targets.

Figure 2:
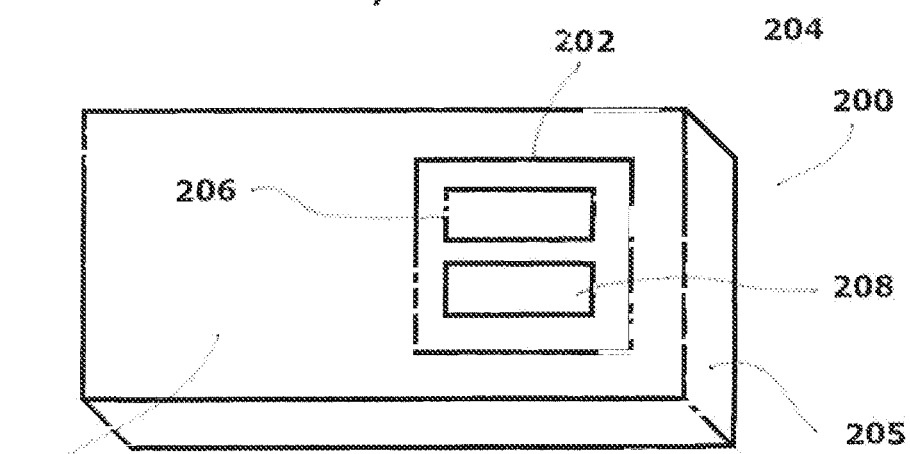
FIG. 2 illustrates an implementation of one exemplary aspect of a calibration target.
Figure 3:
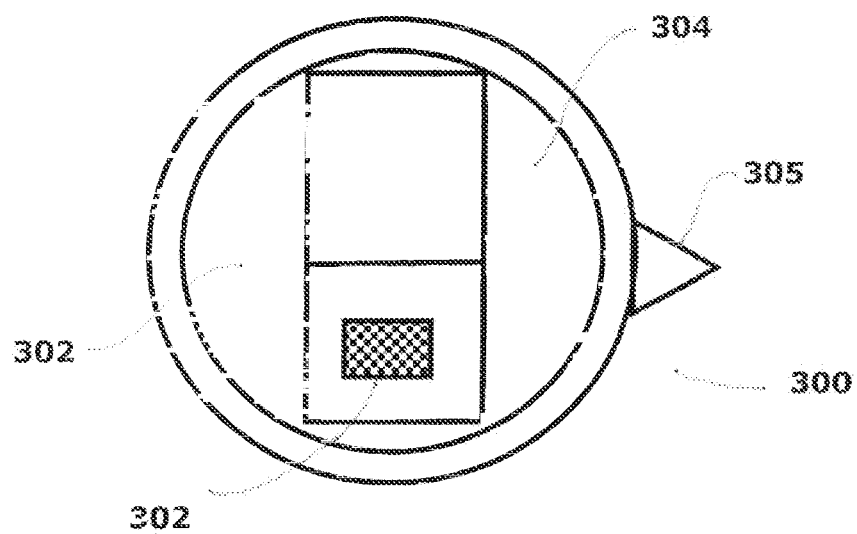
FIG. 3 illustrates an implementation of one exemplary aspect of a calibration target with a plurality of zones, where each zone provides pact of the information needed to calibrate an instrument.

According to the present disclosure and as shown in FIG. 2, a disposable calibration target 200 can be provided. The disposable calibration target 200 can comprise a calibration target region 202 having an instrument interface 204, a tissue interface region 206 and, optionally, a polarized film or coating applied to at least a portion of the calibration target region. In one aspect, a calibration target 200 can be configured for placement within instrument 102 for providing the instrument with calibration data. In an optional aspect, the instrument interface 204 can have a communication feature 205 shaped so as to orient the position of a polarized feature provided on the calibration target to be compatible with any polarization components of the instrument 102. For polarization sensitive instruments, the orientation of the calibration device relative to the instrument can be important, so a communication feature can be configured to fix the position of any polarization vectors with respect to the polarization components in the instrument. In one exemplary aspect, the communication feature can be the overall shape of the calibration target, such as a rectangle. In other exemplary aspects, and as shown in FIG. 3, the communication feature 305 can be a tab extending from the calibration target to selectively positionally fix the target relative to the instrument 102. The calibration target 200 can be encoded with calibration data comprising validation codes, calibration constants or calibration ranges.

In a further aspect, the calibration target 200 can comprise at least two storage modalities 206, 208 comprising image-based code, storage medium, an electrical contact, an optical communication means and spectral information. It is contemplated that the calibration data can be distributed across the at least for storage modalities.

In any of the aspects disclosed herein, the storage medium can be, for example and without limitation, an RFID tag, a computer chip, a memory chip or the like. It is further contemplated that the storage medium can be an RFID tag configured to be interrogated by the instrument. In an even further aspect, the RFID tag can be a read/write RFID tag and the system can be configured to disable the disposable once the data has been read to prevent reuse. Here, the RFID tag can be disabled directly or by preventing the duplication of a validation code made part of the data encryption.

In any instance, once the calibration data of the calibration target 200 are determined at the point of manufacture, the information needed to complete the calibration and validation of the disposable calibration target 200 can be encrypted using any number of commercially available techniques such as, for example and without limitation, Defense Encryption Standard (DFS3), Advanced Encryption Standard (AES), and the like prior to recording the calibration data in at least one of an RFID tag or image-based cede.

In further aspects, the image-based code can comprise a polarization-encoded image-based code. Here, the polarization-encoded image-based code can be configured to conceal the calibration data so it is not visible to the naked eye and can only be detected by polarization sensitive instrumentation. Alternatively, the image-based code can be configured to be visible to the instrument sensors when illuminated with a particular wavelength or range of wavelengths of light. In one aspect, the invisible images described in Proceedings of the international MultiConference of Engineers and Computer Scientists 2009 Vol I IMECS 2009, Mar. 18-20, 2009, Hong Kong can be employed. In another aspect, infrared inks can be employed. In a further aspect, the calibration target can enable a multimodal approach using boat polarizations viewed at the same time or one polarization together with a spectrally specific pattern. The image-based code can be divided between the two polarizations such that one polarization does not contain the entire calibration data set. The calibration data can also be divided between two spectral regions such that one region does not contain the entice calibration data set. In light of the present disclosure, one skilled in the art will appreciate that use of at least two storage modalities, encryption of calibration data or use of spectral or polarization encoded images can conceal calibration or validation information from potential counterfeiters. In further aspects, calibration targets can enable the instrument to read the calibration data and adjust its output based on a combination of the calibration data and the measurement of the calibration target characteristics.

In further aspects, the calibration target can have a plurality of distinct areas configured to accomplish different functions. In one aspect, the calibration target comprises a spectral area configured to be used to calibrate the spectral response of the instrument along with a data image area that comprises calibration data. In a further aspect, the spectral calibration area can be further divided into regions with difference spectral characteristics much as, for example and without limitation, one or more different fluorphores, one or more different scattering responses one or more different polarization responses and the like.

In another aspect that can be illustrated by FIG. 2, a calibration target 200 can further comprise a surface divided into two portions where a first portion 206 is configured to be used by a field instrument to measure its spectroscopic parameters and a second portion containing an image-based code containing the factory-produced calibration data or optional RFID chip encoded with the factory produced calibration data.

In another aspect shown in FIG. 3, a calibration target 300 can further comprise a surface divided into three or more portions where a first portion 302 contains an image-based code encoded with the factory-produced calibration data, a second portion 304 comprises a first spectral target having a first set of spectral characteristics, a third portion 306 comprises a second spectral target having a second set of spectral characteristics and so on. Each second, third and higher portion can comprise at least one of a distinct fluorophore, RF impedance, a distinct scattering response or a distinct polarization response or multiples or combination thereof. Thus, multiple calibration functions can be achieved with one calibration target.

in further and optional aspects, calibration targets having a validation code encoded therein can enable the instrument to accept or reject art inserted calibration target based on, for example and without limitation, unsuitability, past use or other criteria. In one aspect, a validation code can be transmitted to a storage medium provided in the calibration target 200, 300 or coded through an image-based code on at least a portion of the surface of the disposable calibration target in order to identify and authenticate the target. The validation cede stored on the calibration target 200, 300 can be used to verify the source of the calibration target and allow calibration to proceed. Such a validation code can present use of counterfeit, third party or otherwise unsuitable calibration targets. In operation, the instrument 102 can be configured to read the validation code stored on the calibration target 200, 300 when the target has been selectively attached to the instrument. In one aspect, the instrument can read and, if needed, decrypt the validation code and subsequently compare the validation code to, for example and without limitation, a stored list of valid validation codes or an algorithm configured to validate the validation code. In another aspect, the validation code can be encrypted and the instrument 102 can be configured to communicate through a communication means such as, for example and without limitation, a telephone line, the internet and the like. In another aspect, the instrument 102 can comprise an attachable encrypted code module that can be accessed to validate the disposable such as a double 103. Subsequent to a successful validation, the calibration data can be read from the disposable, read from a lookup table or obtained remotely from a central location. It is also contemplated that the calibration target can provide validation information only and does not contain any other calibration data.

In one aspect, a factory-based in can be used to determine the calibration data and the resulting calibration data can be transmitted to a storage medium in the calibrated instrument or ceded through an image-based cede defined on a portion of a calibration target. In one aspect the measured calibration constants can be, for example and without limitation, reflectance, scattering, fluorescence. RF impedance, Raman, polarization and the like; impedance in the case of an RF probe and other modalities known in the art. It is contemplated that at least a portion of the calibration data can be stored in an image-based code defined on a portion of the calibration target readable by the instrument. In another aspect at least a portion of the calibration data can be stored on a storage medium such as, for example and without limitation, an RFID tag or the like. It is also contemplated that the calibration data can be encrypted using any number of commercially available techniques prior to loading into a storage medium or image-based code. In one aspect, in operation, a first portion of the calibration target can be used by the instrument undergoing calibration to measure its own spectroscopic parameters and, subsequently, those measured spectroscopic parameters can then be compared to the factory calibration data read from an image-based code defined on a second portion of the target.

Referring back to FIG. 1, during a calibration procedure, radiation 104 can be transmitted toward a calibration target 200. Optionally, a shield 110 can serve as a barrier between the instrument 107 and a material or tissue 106 to be measured, and can function to reduce potential contamination of the material or tissue 106. Radiation 104 passes through a region and reaches a surface 114 of the calibration target 200. The surface 114 can be the same material as the calibration target 200, or a specially applied layer. The surface 114 can be operable to reflect or scatter radiation back towards the instrument 102, or emit fluorescent or luminescent radiation. The surface 114 can also be configured to transmit at least one of a first and second calibration data to the instrument 102 in response to radiation. Throughout this disclosure, reflection and scattering are used interchangeably and meant to indicate that radiation travels back toward instrument 102. Once the instrument 102 is calibrated, the calibration target 200 can be removed, and the system 100 can be used to take measurements on a target material 106.

In another aspect, a method for calibrating an instrument 102 with a calibration target can be provided. First, the calibration target 200 can be positioned in the instrument 102. Then, the instrument 102 can read the calibration data encoded on the calibration target. If the data is encrypted, the calibration data can then be un-encrypted either in the instrument or through remote access to a decryption routine available through an interact connection or a dongle. Here, the instrument 102 can be configured to communicate through a communication means such as, for example and without limitation, a telephone line, the internet and the like. Alternatively, the instrument 102 can be configured to receive a dongle 103 containing a cede module configured unencrypt the calibration data. Next, the instrument 102 can measure the calibration characteristics of the calibration target 200. The instrument can be configured to then compare the measured characteristics to the stored calibration ranges for the calibration target. Next, the measured characteristics can be compared to the stored acceptable ranges in order to generate a pass-fail indication. If the measured characteristics receive a passing indication, then the instrument can use the measured characteristics and the calibration data to generate a set of calibration constants. The instrument 102 can then use the calibration constants to perform a calibration. Then, optionally, the calibration target 200 can be removed from the instrument prior to use. During a subsequent measurement procedure, at least a portion of surface 114 of the calibration target 200 can be optically transparent, allowing the radiation to reach the material or tissue 106 and the material or tissue 106 to reflect radiation back to the instrument 102.

In another aspect, the instrument 102 can employ existing sensors to read calibration data stored on the calibration target. In one aspect, the sensors can be cameras. In operation, the cameras can be configured to capture an image-based code and extract the calibration data. The image-based code can be defined on the calibration target or ether part of the disposable calibration device. It is contemplated that the image-based code is not be visible to the naked eye in order to prevent counterfeiting. Here, the image-based cede can be configured to only be visible to the sensors when illuminated with a particular wavelength of light. In one aspect, it is contemplated that the image-based code can be printed in an ink visible only under selected conditions, such as, for example and without limitation, fluorescing ink.

In other aspects, the system 100 can be configured to prevent reuse of a calibration target by disabling the storage medium such as an RFID tag. In further aspects, it is contemplated that a read/write RFID tag can be used and subsequently recoded to disable the disposable from subsequent data being read.

In other aspects, the system 100 can be configured to prevent reuse or duplication of a validation code by at least one of rejecting a calibration target having a previously-used validation code; printing the image-based code in a medium that is bleached or destroyed by the radiation of the instrument after a single use, or printing the image-based code in a medium that decays in air subsequent to removal of an airtight covering. As one skilled in the art will appreciate, inks that can be made invisible by exposure to air can include, for example and without limitation, a water-based acid-base indicator that changes from a colored to a colorless solution upon exposure to air and the like. Typical pH indicators for ink can be thymolphthalein (blue) or phenolphthalein (red or pink). The indicators can be mixed into a basic solution that becomes more acidic upon exposure to air, causing the color change. It is contemplated that, in addition to disappearing ink, you could use different indicators to make color-change inks.

In light of the present disclosure one skilled in the art will appreciate that, in the case of an information storage image printed in a medium subject to bleaching by the illumination of the instrument 102, changes in spectral response with time during the bleaching process can be used to validate or calibrate the instrument.

Figure 4:
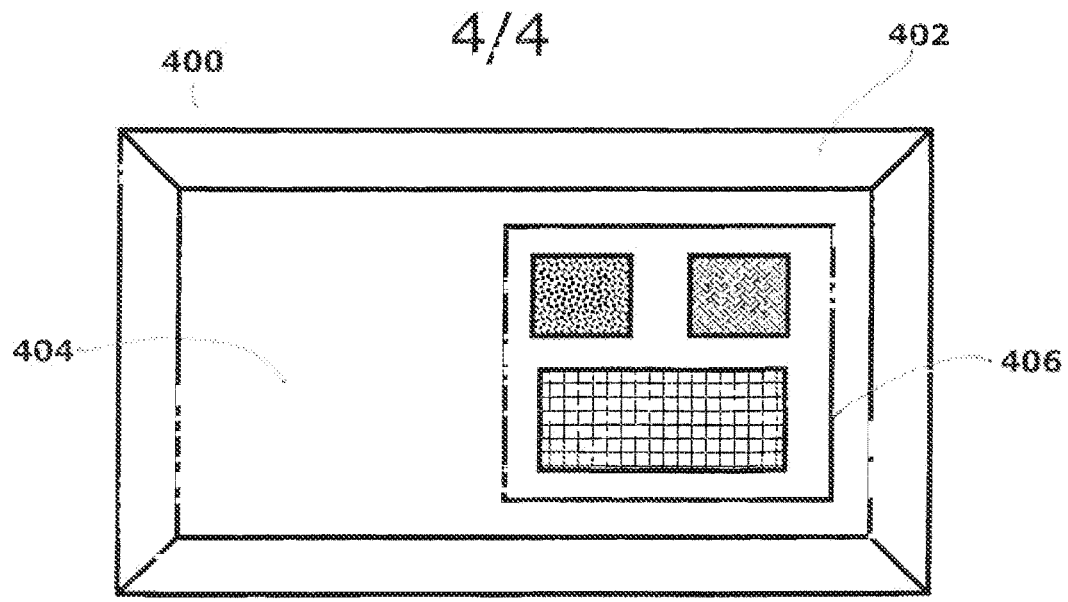
FIG. 4 illustrates an implementation of one exemplary aspect of a pathology tray comprising a calibration target.

In even further aspects of the present disclosure and as shown in FIG. 4, the disposable calibration target can be integrated into a pathology tray 402. The tray 402 can have a window 404 defined in the bottom portion of the tray that corresponds to the sample, patient or tissue interfacing surface. In one illustrative aspect, a tray having dimensions of about 4 inches wide, about 6 inches long and about 1 inch deep can be formed from plastic and have a calibration target disposable 406 removably secured into the bottom over at least a portion of the window 404. In operation, the instrument 102 can be calibrated using the calibration target 406, and, optionally, the calibration target can be removed from the tray 402. Then, a pathology sample can be positioned in the window 404 and the instrument caused to image the pathology sample. In further aspects, the tray itself comprises the instrument interface for the disposable calibration target. Here, the tray can comprise an image-based code or storage medium containing calibration data and appropriate connections to allow the instrument to read the data. In an alternate aspect, the instrument can obtain data from an image placed in its field of view then the tray positioned for calibration and measurement.

In yet other aspects, the tray can have markings configured to record or preserve orientation markings (e.g., superior, inferior, medial, lateral, anterior, posterior) indicating the location and orientation of a tissue sample in the body. The markings can be detected by the instrument so that data collected in automatically recorded as to which side of the sample is being viewed. In practice this is achieved by having a tray with a different zone for each orientation, each zone being appropriately marked to correspond to each orientation and such marking delectable by the instrument. The markings could be as simple as numbers or ever or symbols printed on the tray or an array of lights that illuminate differently for each corresponding orientation.

The advantages of the present disclosure are numerous and will be apparent to one skilled in the art. The calibration targets and related systems and methods can prevent duplication of calibration targets and unauthorized use of the instrument. Calibration targets described herein also eliminate the need to carefully control the spectral characteristics of the calibration target material since data on the exact spectral characteristics expected are encoded into each calibration target.

The present invention can thus be embodied in ether specific forms without departing from its spirit or essential characteristics. The described aspects are to be considered in all respects only as illustrative and not restrictive. The scope of the invention is, therefore, indicated by the appended claims rather than by the foregoing description. All changes that come within the meaning and range of equivalency of the claims are to be embraced within their scope.

I claim:

1. A calibration target, comprising:
   an instrument interface comprising:
      a first storage element having a first set of calibration data encoded therein, and
      a second storage element having a second set of calibration data encoded therein;
      wherein the first storage element is a different type of storage element than the second storage element; and
      wherein both the first and second set of calibration data are required to calibrate an instrument.

2. The calibration target of claim 1, wherein each of the first and second storage elements are selected from the group consisting of an image-based code, an RFID tag, a computer chip, an electrical contact and an optical communication means.

3. The calibration target of claim 1, wherein the first storage element comprises an image-based code.

4. The calibration target of claim 3, wherein the image-based code comprises a first polarization-encoded image-based code.

5. The calibration target of claim 4, wherein the image-based code further comprises a second polarization-encoded image-based code.

6. The calibration target of claim 3, wherein the image-based code is selectively visible under a particular range of wavelengths of light selected to be invisible to the naked eye.

7. The calibration target of claim 3, wherein the image-based code farther comprises a spectrally-encoded image-based code.

8. The calibration target of claim 3, wherein the second storage element comprises an RFID tag.

9. The calibration target of claim 1, wherein each of the first and second set of calibration data comprises at least one of validation data, a calibration constant, and a calibration range.

10. The calibration target of claim 1, wherein the instrument interface comprises a polarized film covering at least a portion thereof.

11. The calibration target of claim 1, wherein the instrument interface comprises a surface divided into first portion and a second portion.

12. The calibration target of claim 11, wherein the first portion is configured to facilitate measurement of the spectral properties of an instrument.

13. The calibration target of claim 11, wherein the second portion contains the first and second storage elements.

14. The calibration target of claim 13, wherein the first storage element comprises an image-based code containing the first set of calibration data encoded therein.

15. The calibration target of claim 14, wherein the second storage element comprises an RFID tag containing the second set of calibration data encoded therein.

16. The calibration target of claim 1, further comprising a pathology tray and wherein the tissue interface and the instrument interface form a portion of the pathology tray.

17. The calibration target of claim 16, wherein at least a portion of the instrument interface is removable subsequent to a calibration operation.

18. The calibration target of claim 1, further comprising a tissue interface.

19. A system, comprising:
   a calibration target comprising:
      a tissue interface; and
      an instrument interface comprising:
         a first storage element having a first set of calibration data encoded therein; and
         a second storage element having a second set of calibration data encoded therein;
         wherein the first storage element is a different type of storage element than the second storage element; and
   an instrument configured to spectrally analyze a tissue sample, the instrument having at least one sensor operable to read calibration data contained on the calibration target and further configured to perform a calibration based on the calibration data;
   wherein both the first and second set of calibration data are required to calibrate of the instrument;
   wherein at least one of the first set of calibration data and the second set of calibration data comprise a validation code; and
   wherein the instrument is further configured to use the validation code to validate the calibration target prior to calibration.

* * * * *